[19] United States Patent
Kojima et al.

[11] 4,167,858
[45] Sep. 18, 1979

[54] REFRIGERANT DEFICIENCY DETECTING APPARATUS

[75] Inventors: Yasuhumi Kojima, Gifu; Teiichi Nabeta, Okazaki, both of Japan

[73] Assignee: Nippondenso Co., Ltd., Kariya, Japan

[21] Appl. No.: 835,898

[22] Filed: Sep. 23, 1977

[30] Foreign Application Priority Data

| Oct. 27, 1976 | [JP] | Japan | 51-129871 |
| Nov. 22, 1976 | [JP] | Japan | 51-156912[U] |
| Nov. 30, 1976 | [JP] | Japan | 51-160707[U] |
| Apr. 22, 1977 | [JP] | Japan | 52-51562[] |
| Apr. 22, 1977 | [JP] | Japan | 52-51563[U] |
| May 6, 1977 | [JP] | Japan | 52-52315 |
| May 6, 1977 | [JP] | Japan | 52-52316 |

[51] Int. Cl.$^2$ ............ F25B 49/00; G01K 13/00; F25B 41/04
[52] U.S. Cl. ............ 62/126; 62/129; 62/228
[58] Field of Search ............ 62/126, 129, 228; 417/32

[56] References Cited

U.S. PATENT DOCUMENTS

| 2,082,035 | 6/1937 | Smith | 62/129 |
| 2,621,487 | 12/1952 | Warren | 62/126 X |
| 2,826,044 | 3/1958 | Roer | 62/129 X |
| 3,059,443 | 10/1962 | Garner | 62/129 X |
| 3,165,569 | 7/1965 | Obermaier | 62/129 |
| 3,225,555 | 12/1965 | Chatlos | 62/129 |
| 3,271,971 | 9/1966 | Jensen et al. | 62/228 |
| 3,363,429 | 1/1968 | Wechsler et al. | 62/228 X |
| 3,411,310 | 11/1968 | Caldwell | 62/228 X |
| 3,412,570 | 11/1968 | Prueh, Sr. | 62/228 X |
| 3,695,054 | 10/1972 | Barry | 62/228 X |
| 3,702,064 | 11/1972 | Ciolli | 62/228 X |
| 3,707,851 | 1/1973 | McAshan, Jr. | 62/129 X |
| 3,846,730 | 11/1974 | Hamilton | 62/129 X |
| 3,959,980 | 6/1976 | Hamilton | 62/126 |
| 4,008,755 | 2/1977 | Vandamme | 62/129 X |

FOREIGN PATENT DOCUMENTS 48-35861 10/1973 Japan .

Primary Examiner—Leslie Braun
Attorney, Agent, or Firm—Cushman, Darby & Cushman

[57] ABSTRACT

In the pipeline of a refrigerator system comprising a compressor, a condenser, an expansion valve and an evaporator, a thermistor adapted to serve as a detector for detecting the dryness of refrigerant is disposed so as to be immersed in the refrigerant at a position where the refrigerant is changed into a homogeneous gas-liquid mixture under the low refrigerant condition. The dryness of the refrigerant is detected by utilizing the fact that while the thermistor is cooled by the refrigerant when its quantity is normal, when its quantity is below normal the refrigerant is changed into a dry gas so that the thermistor is not cooled by the refrigerant and its resistance value is changed. Also a control circuit is provided which is responsive to the signal from the detector, whereby when the dryness of the refrigerant reaches a predetermined value, a signal is generated to render the compressor inoperative. This ensures accurate detection of the shortage of refrigerant and has the effect of preventing failure of the compressor due to the compressor being operated with the insufficient refrigerant.

8 Claims, 11 Drawing Figures

REFRIGERANT DEFICIENCY DETECTING APPARATUS

BACKGROUND OF THE INVENTION

The present invention relates to a low refrigerant detecting apparatus for refrigerators, e.g., automobile air conditioning systems.

With a refrigerator of the type which is not provided with any special protective means against the leakage of refrigerant, there is the danger of the refrigerator being operated with the insufficient refrigerant. The problem with this is that the lubricating oil of the compressor is retained, for example, in the receiver in the refrigerating cycle, thus causing burning of the compressor. Particularly, with a refrigerator of the type in which the evaporation pressure regulating valve is provided on the low pressure side, leakage of the refrigerant causes the regulating valve to close, thus further aggravating the problem.

To overcome this difficulty, an apparatus has been proposed in Utility Model Publication No. 48-35861 which was published on Oct. 27, 1973 in Japan and assigned to the same assignee as that of the present application. The apparatus includes a semiconductor device whose resistance is changed by its self-heating and which is positioned between the condenser and the expansion valve and immersed in the liquid refrigerant in the receiver which collects the refrigerant in liquid form, whereby when the quantity of the liquid refrigerant becomes less than a predetermined value, the semiconductor device comes out of the liquid refrigerant and the degree of its cooling decreases, thus causing its resistance value to change by an amount smaller than a predetermined value and thereby generating a signal.

With this apparatus, whenever the liquid refrigerant in the receiver is exhausted, it always results in the generation of a signal. This gives rises to a problem from a practical point of view in that such condition does not always mean the complete loss of the cooling capacity, and there are cases where the refrigerating system is rendered inoperative despite the fact that the refrigerating system still retains its cooling capacity.

Further, since the liquid level of the liquid refrigerant in the receiver is changed by the rotational speed of the compressor, the heat load related to the inlet temperature of the evaporator, etc., there is the danger of generating a warning signal irrespective of the excess and deficiency of the refrigerant in liquid form.

SUMMARY OF THE INVENTION

It is an object of the present invention to provide an improved apparatus which is capable of positively detecting the shortage of refrigerant.

It is another object of the invention to provide a control system for refrigerator systems which is so designed that the compressor is rendered inoperative only when the point is reached where the refrigerating capacity has been completely lost, thus impeding the lubrication of the compressor.

It is a further object of the invention to provide a control system for refrigerator systems wherein a detector comprising a self-heating type thermistor or the like is disposed, for example, in the pipeline between the receiver and the evaporator, whereby when the refrigerant quantity which would normally be 800 grams is reduced to about 200 grams, a change in the heat capacity of the refrigerant caused by a change in the gas-liquid ratio of the refrigerant flowing in the pipeline, is detected by a change in the temperature of the probe of the detector and an electric signal is generated to stop the compressor.

It is a still further object of the invention to provide an improved structure which permits easy mounting in the pipeline of a refrigerator system of a detector adapted to detect the shortage of refrigerant in accordance with the degree of dryness of the refrigerant.

DESCRIPTION OF THE PREFERRED EMBODIMENTS

Figure 1:
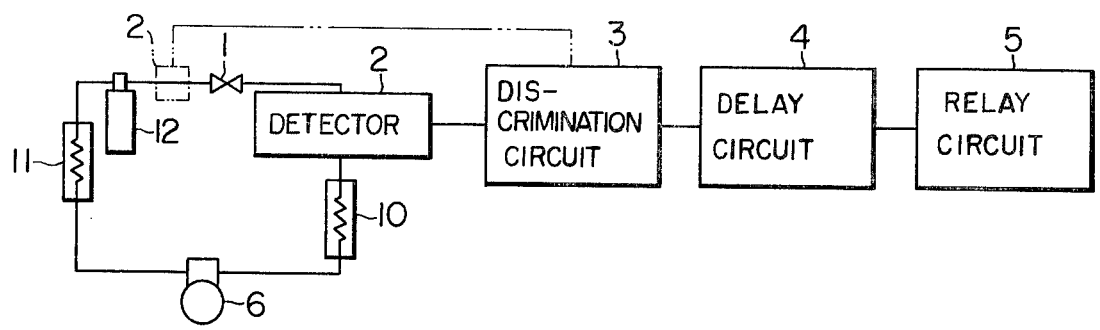
FIG. 1 is a schematic diagram showing the general construction of a refrigerator system incorporating a detecting apparatus according to the invention.
Figure 2:
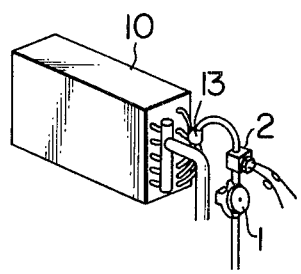
FIG. 2 is a perspective view showing the manner of mounting the detector shown in FIG. 1.
Figure 3:
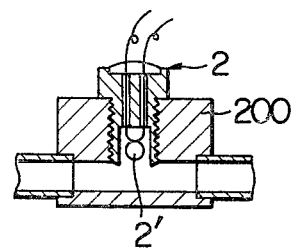
FIG. 3 is a sectional view of the detector mounted in the manner shown in FIG. 2.

The present invention as applied for illustrative purposes to a refrigerator system, e.g., an automobile air conditioning system will now be described. As shown in FIG. 1, the detecting apparatus of this invention comprises a detector 2 for detecting the dryness of the refrigerant at the outlet of an expansion valve 1 in the air conditioning system, a dryness discrimination circuit 3 for discriminating whether the dryness at the expansion valve outlet is higher or lower than a predetermined dryness, a delay circuit 4 designed so that when the refrigerant dryness exceeds the predetermined value and remains so in excess of a predetermined time an output signal is generated to operate a relay circuit 5, and the relay circuit 5 for stopping the operation of a compressor 6 or lighting an indicator lamp. As shown in FIG. 2, the detector 2 is disposed in the pipeline downstream of the expansion valve 1 and upstream of the distributor of an evaporator 10 which will be described later. The detector 2 includes a thermistor 2' (FIG. 3) and it detects the dryness of the refrigerant by utilizing the fact that the thermistor 2' is cooled by the refrigerant when its quantity is normal, whereas when the refrigerant is short so that the refrigerant is changed into a gas the thermistor 2' is not cooled and its resistance value changes. In other words, the thermistor 2' detects the dryness of the refrigerant by detecting through its resistance value a change in the temperature of the thermistor 2' caused by a change in the heat capacity due to a change in the refrigerant quantity. As shown in FIG. 3, the thermistor 2' is positioned in a secluded portion outside the inner diameter of the pipe of the pipeline downstream of the expansion valve 1 and thus the refrigerant flow is prevented from directly impinging on the thermistor 2'.

In FIG. 1, the evaporator 10 is so designed that the refrigerant subjected to a diabatic expansion by the expansion valve 1 is evaporated thus cooling the air and hence the passenger room of the automobile. Numeral 11 designates a condenser for condensing the refrigerant compressed by the compressor 6, 12 a receiver for storing the refrigerant flowing thereinto from the condenser 11.

While, in the embodiment described above, the refrigerant dryness is detected in the pipeline portion downstream of the expansion valve 1 and upstream of the evaporator 10, it is possible to detect the shortage of refrigerant by detecting the dryness of the refrigerant in the portion upstream of the expansion valve 1 and downstream of the condenser 11, more particularly in the portion upstream of the expansion valve 1 and downstream of the receiver 12. Further, while, in the embodiment described above, the refrigerant dryness is detected by the thermistor 2' in terms of the change in the heat capacity, it is also possible to detect the refrigerant dryness optically by mounting for example a photo emitter and photo receiver in a portion of the refrigerator pipelines and utilizing the fact that the transmittance or refractive index of light through the refrigerant is changed in accordance with the dryness of the refrigerant.

Figure 5:
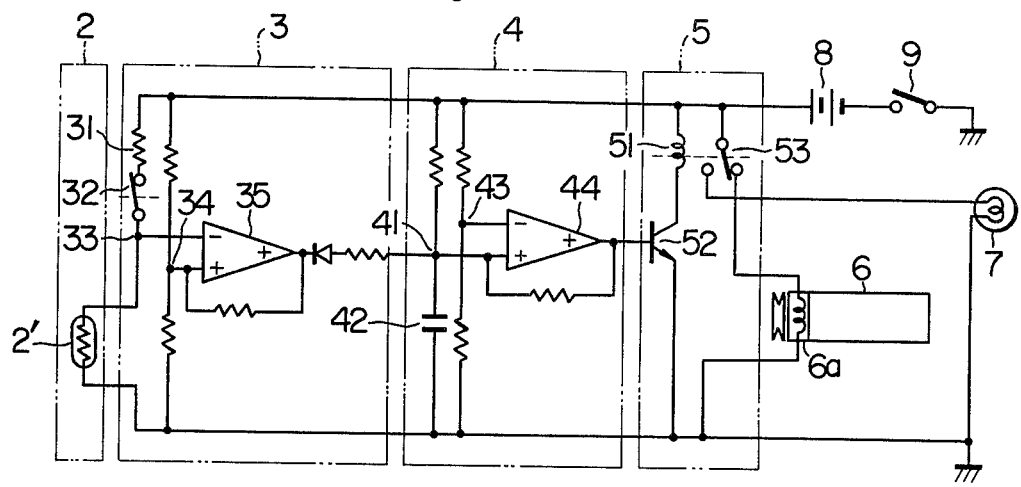
FIG. 5 is a circuit diagram of the control circuit section shown in FIG. 1.

The construction and operation of the apparatus according to the invention will now be described in greater detail. As shown in FIGS. 1, 2 and 5, the apparatus of this invention comprises the detector 2 including a self-heating type thermistor which detects, in terms of a temperature change, the dryness of the refrigerant in the pipeline between the outlet of the expansion valve 1 and the evaporator 10, and the control circuit section including the discrimination circuit 3 responsive to the detection signal from the detector 2 for discriminating whether the refrigerant dryness is higher or lower than a predetermined dryness, the delay circuit 4 responsive to the signal from the discrimination circuit 3 for generating an output signal and operating the relay circuit 5 when the refrigerant dryness exceeds the predetermined value and remains so in excess of a predetermined time and the relay circuit 5 for lighting an indicator lamp 7 constituting a warning device and stopping the current supply to the thermistor 2' of the detector 2. As shown in FIG. 3, the detector 2 includes a pipeline coupling 200 having a recess formed in the central portion of its pipeline joining passage and mounted in the pipeline, and the thermistor 2' having a negative temperature coefficient of resistance is mounted in the recess so as to prevent the refrigerant flow from directly impinging on the thermistor 2'. Numeral 8 designates a power source. In FIG. 2, a distributor 13 is adapted to distribute the refrigerant into the plural tubes of the evaporator 10.

Figure 4:
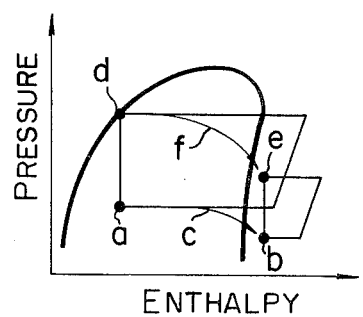
FIG. 4 is a Mollier diagram of a refrigerating cycle.

With the construction described above, the operation of the apparatus is as follows. As shown in FIG. 5, the thermistor 2' is connected in series with a resistor 31 and relay contacts 32, and the relay contacts 32 are contacts which are opened and closed by a relay 51 of the relay circuit 5 which will be described later so that the relay contacts 32 are opened when the refrigerant is short thus energizing the relay 51. Since the relay contacts 32 are normally closed, the thermistor 2' is energized and it tends to generate heat by itself. However, if, in this case, the normal quantity of the refrigerant is present, the refrigerant at the outlet of the expansion valve 1 is in the state indicated at a in the Mollier diagram of FIG. 4, namely, the refrigerant is in gas-liquid mixture form having a nearly zero dryness and a high specific heat, thus properly cooling the thermistor 2' and thereby impeding its heat generation. Consequently, the internal resistance of the thermistor 2' increases and a high potential is maintained at a junction point 33 in the discrimination circuit 3 shown in FIG. 5. On the contrary, when the refrigerant is short, the refrigerant is changed from the state a into a state b as indicated by an arrow c in FIG. 4, namely, the refrigerant is changed to a gas state having a low specific heat with the result that the amount of the heat generated by the thermistor 2' increases and its internal resistance decreases. This decreases the potential at the junction point 33 of the discrimination circuit 3, so that the potential eventually becomes lower than that at a junction point 34 and a comparator 35 is now noninverting. Consequently, the potential at a junction point 41 of the delay circuit 4 is changed from a low potential to a high potential and a capacitor 42 starts to charge. When this condition continues a predetermined time so that the potential at the junction point 41 becomes higher than a reference potential point 43, a comparator 44 becomes noninverting so that the base potential of a transistor 52 in the relay circuit 5 is increased and the transistor 52 is turned on. When this occurs, the relay 51 is energized so that relay contacts 53 stop the current flow to a magnetic clutch 6a of the compressor 6 and cause the indicator lamp 7 to go on thus giving a warning. In addition, by virtue of the fact that the relay 51 opens, as mentioned previously, the relay contacts 32 adapted for energizing the thermistor 2', the heat generation of the thermistor 2' is stopped thus protecting it. The potential at the junction 32 is then reduced to the ground potential, with the result that the comparator 35 of the discrimination circuit 3 remains in the noninverting condition and it discriminates in the same manner as that under the low refrigerant condition, thus preventing the compressor 6 from coming into operation again.

While, in the above-described embodiment, the detector 2 employing the thermistor 2' for detecting the shortage of refrigerant, is disposed between the outlet of the expansion valve 1 and the evaporator 10, as shown by the dotted line in FIG. 1, the amount of refrigerant can also be detected by disposing the detector at a position upstream of the expansion valve 1 and the downstream of the receiver 12 to detect the change in the state (the change in the dryness) of the refrigerant. In this case, while the refrigerant in the high pressure pipeline is normally in a liquid state indicated at d in the Mollier diagram of FIG. 4, when its quantity is less than normal the refrigerant changes, as shown by an arrow f, into a gas state indicated at e and having a low specific heat. Thus, the shortage of refrigerant can be detected in the similar manner as in the above-described embodiment.

Figure 6:
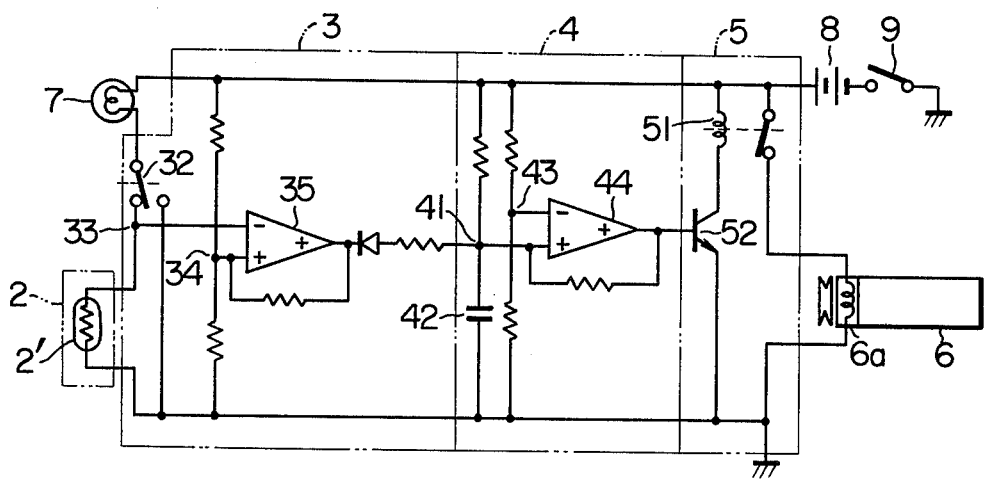
FIG. 6 is a variation of the circuit diagram for the control circuit section.
Figure 7:
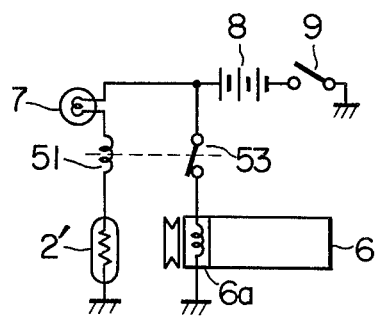
FIG. 7 is a circuit diagram showing another embodiment of the apparatus of the invention.

FIG. 6 shows still another embodiment of the apparatus of this invention, which differs from the embodiment of FIG. 5 in that the resistor 31 of the discrimination circuit 3 is replaced by the indicator lamp 7. While, in this embodiment, with the refrigerant being short the compressor 6 is stopped and the indicator lamp 7 is lighted thus giving a warning as in the case of the embodiment shown in FIG. 5, the relay contacts 32 of the discrimination circuit 3 which are operable by the relay 51 of the relay circuit 5, are so designed that when the refrigerant is short the relay contacts 32 are connected to a ground terminal so that the indicator lamp 7 is caused to continuously give a warning and no current is supplied to the thermistor 2'. It is to be noted that if the detector uses a thermistor having a sufficiently high current capacity, the thermistor 2' may be directly connected to the indicator lamp 7 and the relay 51 as shown in FIG. 7. This circuit is simplified in construction in that the amplifier circuit between the thermistor 2' and the indicator lamp 7 is eliminated.

Figure 8:
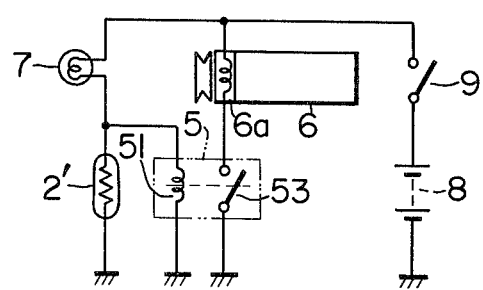
FIG. 8 is a circuit diagram showing still another embodiment of the apparatus of the invention.

FIG. 8 shows still another embodiment of the apparatus of this invention, which differs from the previously described embodiments in that no amplifier circuit is provided between the thermistor and the indicator lamp, that the thermistor is connected in parallel with the relay circuit, and that the thermistor has a critical resistance point so that its resistance value decrease rapidly when a predetermined temperature is reached. The thermistor 2' has a negative temperature coefficient of resistance so that while its resistance value remains substantially constant until a certain temperature is reached, the resistance value rapidly decreases at that temperature and thereafter the resistance remains substantially constant. When the amount of the refrigerant is normal during the refrigerating cycle of the refrigerator system, in the pipeline downstream of the expansion valve 1 and upstream of the evaporator 10 the refrigerant is changed to gas-liquid mixture state with its dryness close to zero so that even though current flows to the thermistor 2' causing it to generate heat, the thermistor 2' is fully cooled by the liquid refrigerant thus maintaining its temperature low. Consequently, the resistance value of the thermistor 2' increases so that a sufficient current flows in the relay coil 51 connected in parallel with the thermistor 2' and the relay contacts 53 are closed. Thus, the refrigerator system operates normally. On the other hand, the indicator lamp 7 is not lighted due to the high resistance value of the thermistor 2'.

On the contrary, when the refrigerant quantity drops below normal due to leakage of the refrigerant or the like, in the pipeline between the expansion valve 1 and the evaporator 10 the refrigerant is changed to a gas state with its dryness close to 1, so that the thermistor 2' is cooled to a lesser degree and thus its temperature increases. When the thermistor 2' reaches a predetermined temperature so that its resistance value decreases greatly, the current flow in the relay coil 51 is decreased, thus deenergizing it and thereby opening the relay contacts 53. Thus, when the refrigerant is short, the magnetic clutch 6a is deenergized and the operation of the compressor 6 is stopped, thus preventing damage, e.g., burning of the compressor 6. At the same time, the decreased resistance value of the thermistor 2' increases the current flow in the indicator lamp 7, thus lighting the lamp 7 and thereby informing the driver of the fact that the refrigerant quantity is less than normal.

Figure 9:
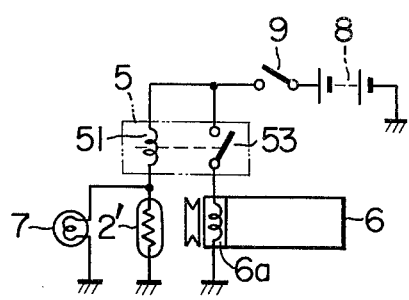
FIG. 9 is a circuit diagram showing still another embodiment of the apparatus of the invention.

FIG. 9 shows still another embodiment of the apparatus of this invention, which differs from the previously described embodiment in that the detector uses a thermistor of positive resistance-temperature characteristic having a critical resistance point, that the thermistor is connected in series with the relay coil and that no amplifier circuit is included.

When the refrigerant quantity is normal, the refrigerant is in gas-liquid mixture form with its dryness close to zero. Consequently, even though current flows in the thermistor 2' of positive characteristic causing it to generate heat, the thermistor 2' is fully cooled by the liquid refrigerant and its temperature is maintained low. As a result, the resistance value of the thermistor 2' decreases so that a sufficient current flows in the relay coil 51 connected in series with the thermistor 2' of positive characteristic and the normally open contacts 53 are closed, thus allowing the refrigerator system to operate normally.

On the contrary, when the refrigerant quantity drops below normal due to leakage of the refrigerant or the like, the refrigerant is changed to a gas state, so that the thermistor 2' is cooled to a lesser degree and the thermistor 2' of positive characteristic increases its temperature. When the temperature of the thermistor 2' reaches the temperature of the predetermined critical resistance point, the resistance value of the thermistor 2' rapidly increases with the result that the current flow in the relay coil 51 is decreased greatly and the normally open contacts 53 are returned to the open position. Thus, when the refrigerant quantity is below normal, the current supply to the magnetic clutch 6a is interrupted and the operation of the compressor 6 is stopped. On the other hand, the indicator lamp 7 is connected in parallel with the thermistor 2' of positive characteristic. When the refrigerant is short, the operation of the compressor 6 is stopped and at the same time the indicator lamp 7 is lighted to alert the driver that the refrigerant has become short.

Figure 10:
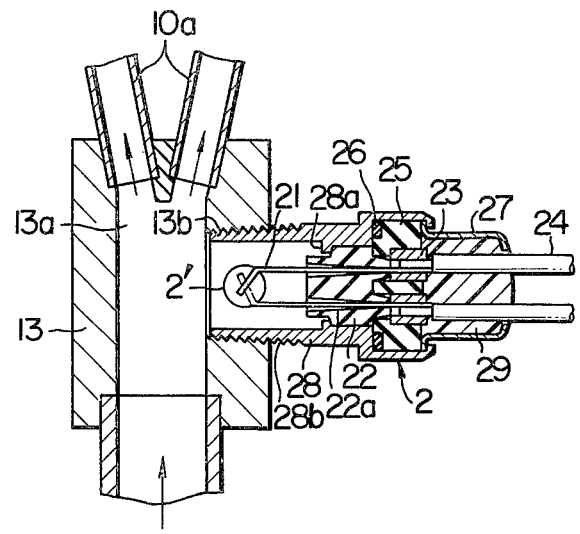
FIG. 10 is a sectional view of the detector mounted integral with the refrigerant distributor.

FIG. 10 shows a modification of the detector 2 which is mounted integral with the refrigerant distributor 13 to detect the dryness of the refrigerant at the outlet of the expansion valve 1. The refrigerant distributor 13 is mounted between the outlet side of the expansion valve 1 and the inlet side of the evaporator 10 to distribute the refrigerant into a plurality of tubes 10a of the evaporator 10, and the detector 2 is mounted integral with the refrigerant distributor 13 to detect the dryness of the refrigerant in a passage 13a of the refrigerant distributor 13. A detailed construction of the detector 2 will now be described with reference to FIG. 10. The detector 2 includes a thermistor 2' having a negative resistance-temperature characteristic, and the thermistor 2' is disposed so as to be exposed to the passage 13a of the refrigerant distributor 13. Lead wires 21 of the thermistor 2' are inserted into brass metallic tubes 23 through openings 22a of a rubber bushing 22, and each lead wire 21 is soldered to one end of a covered lead wire 24 in the metallic tube 23. The two metallic tubes 23 are formed by insert molding within an insulator 25 made of phenolic resin or the like, and the insulator 25 is fixedly mounted, along with a metallic cover 27, to a metallic housing 28 by caulking through an O-ring 26. The rubber bushing 22 is held between a projection 28a and the insulator 25 and fixedly mounted to the inner surface of the housing 28 to hold the lead wires 21 in place and thereby serve the purpose of preventing the thermistor 2' from contacting the housing inner surface by vibrations. A filler 29 consists of a resin such as epoxy resin, and the filler 29 is injected, after the metallic cover 27 has been fitted in place, into the cover 27 where the filler is hardened thus holding the covered lead wires 24 in place and providing a sealing. The metallic housing 28 is provided on its outer surface with a taper external thread 28b so that the detector 2 is hermetically fixedly mounted to the refrigerant distributor 13 by threadedly fitting the taper external thread 28b in a taper internal thread 13b of the refrigerant distributor 13.

As will be seen from FIG. 10, the thermistor 2' is located in a secluded portion outside the inner diameter of the passage 13a of the refrigerant distributor 13, and in this way the refrigerant flow is prevented from directly impinging on the thermistor 2'.

The housing 28 of the detector 2 may be hermetically fixedly mounted to the refrigerant distributor 13 by a straight thread through an O-ring.

Further, the detecting means included in the detector 2 is not limited to the thermistor 2' of negative characteristic, and it is possible to use any other temperature sensitive device, e.g., a thermistor having a positive resistance-temperature characteristic so that its resistance value rapidly increases at a predetermined temperature.

Furthermore, the fact that the detector 2 is mounted integral with the refrigerant distributor 13 has the effect of eliminating the need to additionally provide a mounting block or the like in the refrigerant pipeline and thereby making the detector 2 compact and simple in construction and reducing the cost.

Figure 11:
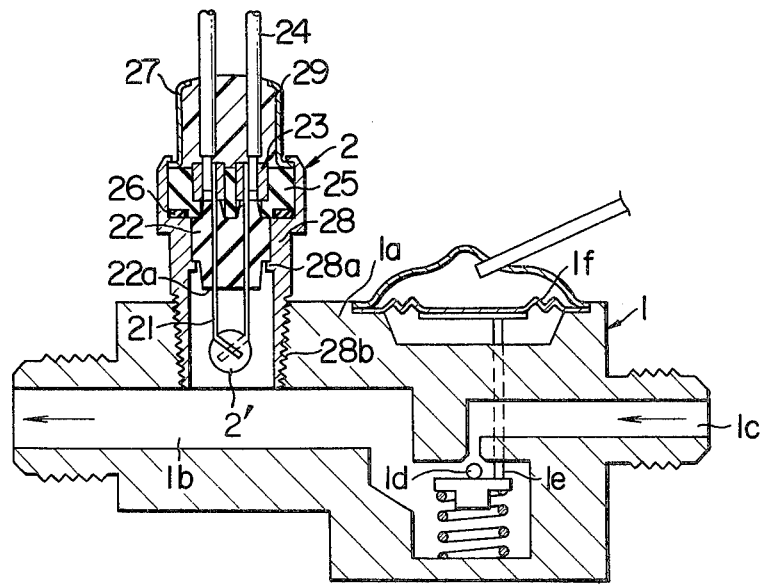
FIG. 11 is a sectional view of the detector mounted integral with the expansion valve.

FIG. 11 shows another modification of the detector which is mounted integral with the expansion valve. The detector 2 is integrally mounted to a housing 1a of the expansion valve 1. Referring to FIG. 11 showing a detailed construction of the detector 2, the detector 2 includes a thermistor 2' having a negative resistance-temperature characteristic, and the thermistor 2' is disposed so as to be exposed to an outlet side passage 1b of the expansion valve 1. The remaining construction of the detector 2 is the same as that of the detector 2 shown in FIG. 10. Thus, the taper external thread 28b in the outer surface of the metallic housing 28 is threadedly fitted in a taper inner thread 1a' of the expansion valve housing 1a, thereby hermetically fixedly mounting the detector 2 to the expansion valve housing 1a.

The expansion valve 1 comprises a valve member 1d positioned between an inlet passage 1c and the outlet passage 1b, and the valve member 1d is movable through a shaft 1e in response to the displacement of a diaphragm 1f which in turn is adapted to be displaced in accordance with the change in the degree of superheat of the refrigerant at the outlet side of the evaporator 10. As shown in FIG. 11, the thermistor 2' is disposed in a secluded position outside the inner diameter of the outlet side passage 1b of the expansion valve 1, and in this way the refrigerant is prevented from directly impinging on the thermistor 2'.

Alternately, the housing 28 of the detector 2 may be hermetically fixedly mounted to the housing 1a of the expansion valve 1 by means of a straight thread through an O-ring.

Further, the detector 2 may be mounted to a unit in which the expansion valve 1 and the evaporation pressure regulating valve are integrally mounted in the same housing.

Still further, the detecting means included in the detector 2 is not limited to the ordinary thermistor 2' having a negative-resistance characteristic, and any other thermally sensitive resistance element such as a thermistor having a positive temperature-coefficient characteristic whose resistance value rapidly increases at a predetermined temperature may be used.

The fact that the detector 2 is integrally mounted to the expansion valve 1 has the effect of eliminating the need to additionally provide a mounting block or the like in the refrigerant pipeline and thereby making the detector 2 compact and simple in construction and reducing the cost.

We claim:

1. A refrigerant deficiency detecting apparatus for a refrigerator system including a refrigerant, a compressor, a condensor, a receiver, an expansion valve and an evaporator, said apparatus comprising:

a d.c. electric source;

a temperature responsive resistor element positioned in the refrigerator system between said receiver and evaporator for changing its resistance in response to changes in the cooling effect of said refrigerant;

a current limiting resistor;

normally closed switch means for selectively effecting a series connection between said current limiting resistor and said temperature responsive resistor across said d.c. electric source to provide a temperature responsive d.c. voltage signal at the junction point of said switch means and said temperature responsive resistor;

a comparator circuit connected to said junction point for generating a discrimination signal either when said temperature responsive d.c. signal exceeds a predetermined value or when said normally closed switch means is opened;

a delay circuit connected to said comparator for generating a command signal when said discrimination signal continues to exist for a predetermined time; and control means, connected to said delay circuit for rendering said compressor inoperative and for opening said normally closed switch means in response to said command signal.

2. An apparatus as set forth in claim 1 further comprising a heating element placed in said refrigerant.

3. An apparatus as set forth in claim 1 wherein said temperature responsive resistor is a self-heating thermistor.

4. An apparatus as set forth in claim 3, wherein said refrigerator system further includes pipeline coupling means, disposed between said receiver and said evaporator and having a recess formed in the central portion thereof, for joining pipelines adapted to direct said refrigerant from said receiver to said evaporator, and wherein said thermistor is disposed in said recess to prevent the flow of said refrigerant from directly impinging upon said detector.

5. An apparatus as set forth in claim 4, wherein said pipeline coupling means further includes said expansion valve integrally mounted therein.

6. An apparatus as set forth in claim 4, wherein said pipeline coupling means further includes a refrigerant distributor integrally provided therein, said refrigerant distributor being positioned between said expansion valve and said evaporator.

7. An apparatus as set forth in claim 1, wherein said temperature responsive resistor element is made integral with said expansion valve.

8. A refrigerant deficiency detecting apparatus according to claim 1 wherein said current limiting resistor comprises an indicating lamp and wherein said apparatus further comprises a normally open switch for connecting said lamp to said d.c. electric source when said normally closed switch means is opened.

* * * * *